United States Patent [19]

Tarnopolsky

[11] Patent Number: 5,032,247
[45] Date of Patent: Jul. 16, 1991

[54] METHOD AND APPARATUS FOR ELECTROPHORETIC SEPARATIONS

[75] Inventor: Yuri Tarnopolsky, Narragansett, R.I.

[73] Assignee: Separations Technology, Inc., Wakefield, R.I.

[21] Appl. No.: 407,173

[22] Filed: Sep. 14, 1989

[51] Int. Cl.$^5$ ............................................. B01D 13/02
[52] U.S. Cl. .............................. 204/299 R; 204/180.1; 204/182.3
[58] Field of Search ............... 204/299 R, 182.3, 180.1

[56] References Cited

U.S. PATENT DOCUMENTS

| | | | |
|---|---|---|---|
| 3,231,485 | 1/1966 | Kuwata et al. | 204/180 |
| 3,330,749 | 7/1967 | Kuwata et al. | 204/180 |
| 3,533,935 | 10/1970 | Steere et al. | 204/299 R |
| 3,620,958 | 11/1971 | Dijksterhuls | 204/299 R |
| 3,773,645 | 11/1973 | Nees et al. | 204/299 R |
| 3,867,271 | 2/1975 | Hoefer | 204/182.8 |
| 3,901,780 | 8/1975 | Denckla | 204/183.2 |
| 3,941,678 | 3/1976 | Akiyama | 204/299 R |
| 3,948,753 | 4/1976 | Arlinger | 204/299 R |
| 4,177,130 | 12/1979 | Herrmann et al. | 204/299 R |
| 4,284,491 | 8/1981 | Vesterberg | 204/299 R |
| 4,305,799 | 12/1981 | Schwarz et al. | 204/182.1 |
| 4,479,861 | 10/1984 | Hediger | 204/182.8 |
| 4,588,492 | 5/1986 | Bier | 204/301 |
| 4,608,146 | 8/1986 | Penaluna | 204/299 R |
| 4,680,201 | 7/1987 | Hjerten | 427/230 |
| 4,699,706 | 10/1987 | Burd et al. | 204/301 |
| 4,708,782 | 11/1987 | Andresen et al. | 204/299 R |
| 4,747,919 | 5/1988 | Anderson | 204/182.8 |
| 4,769,141 | 9/1988 | Couillard | 210/198.2 |
| 4,816,123 | 3/1989 | Ogan et al. | 204/183.3 |

OTHER PUBLICATIONS

Abstract-pp. 146-146, This relates to U.S. Pat. No. 4,588,492, issued May 13, 1986.
Chemical Abstract, vol. 92, p. 26.
Electrophoresis Magazine, 1985, vol. 6, pp. 377, 381, Miller et al., "Effect of Conductivity and Concentration on the Sample Stream in the Traverse Axis of a Continuous Flow Electrophoresis Chamber."
Separation Science, 2(3), "Continuous Particle Electrophoresis: A New Analytical and Preparative Capability," Allen Strickler, 1967, pp. 335-355.
LC-GC, vol. 3, No. 6, "Bio Separations Technology—Presentations on High Performance Electrophoresis at the 1988 Pittsburgh Conference," pp. 484, 488 and 490-491.
Genetic Engineering News, Mar. 12, 1989 "Washington State University Researcher Develops Novel Electrophoresis Chamber".

Primary Examiner—John F. Niebling
Assistant Examiner—Isabelle R. McAndrews
Attorney, Agent, or Firm—Donald Brown

[57] ABSTRACT

A method and apparatus for conducting electrophoretic separations is described in which heat exchange fluid is passed through hollow fibers in the electrophoretic chamber during the separation process and the separations are conducted in the interstices of the hollow fiber. Hollow fibers made of organic polymers, inorganic materials such as glass and silica, and natural fibers may be used.

9 Claims, 2 Drawing Sheets

METHOD AND APPARATUS FOR ELECTROPHORETIC SEPARATIONS

The present invention relates to electrophoresis. More particularly, the present invention relates to utilization of electrophoresis with controlled cooling. Still more particularly the invention relates to a method and apparatus for separating chemical components in a solution in both a batch and a continuous mode.

BACKGROUND OF THE INVENTION

The process of electrophoresis has gained notoriety in recent years as a method of performing difficult separations, particularly separations involving organic materials in solutions. Thus, in biochemical applications, for example, organic compounds such as peptides, proteins, nucleic acids, antibodies and the like may be separated in solutions containing them by the utilization of electrophoretic techniques. These techniques have generally involved the utilization of columns having tubes and packing and applying electrical charges to the tubes to electrically move the components of the solution and separating them based on their electrophoretic mobility. A typical patent describing such a separation is U.S. Pat. No. 3,533,935.

In a similar vein attempts have been made to utilize capillary tubes for the purpose of conducting the electrophoretic separation. In these processes the separation is conducted inside of the tube. Typical examples of such operations are those described in U.S. Pat. No. 3,620,958 and U.S. Pat. No. 3,941,678.

One of the more serious problems encountered in conducting electrophoretic separations on a larger scale is the generation of heat caused by the electrical current passing across the tube or vessel filled with the electrolyte in which the electrophoresis is taking place. This requires special cooling techniques and a patent describing the problem associated with cooling and one system for conducting cooling is described in U.S. Pat. No. 4,177,130.

In order to overcome convection, various anti-convective media are used such as gels and porous membranes.

Gel electrophoresis has been utilized in the art by employing gels in an array of individual tubes. In general, these processes are of a batch nature and a typical process is shown in U.S. Pat. No. 4,747,919.

Porous membranes were used in PCT International application 7900,942 for the purpose of preventing convection and streamlining the flow of the liquid in an electrophoretic separation.

However, anti-convective media make cooling inefficient and difficult. For this reason the liquid undergoing separation is cooled typically outside the electrophoretic chamber, as shown in this PCT application.

While the prior art has successfully demonstrated that electrophoresis can be conducted and that solutions containing multiple components can be separated utilizing these methods, difficulty has been encountered in translating that technology to a continuous phase operation so that the separations can be conducted continuously with the recovery of the components of a given solution being made on a continuous basis. Further, in scaling up prior art processes the art faces a major problem in that considerable heat which is generated has to be dealt with effectively. If it is not, the separations attempted will not be effective due to the generation of convective currents in the electrophoretic chamber. Further, in the case of solutions containing thermally sensitive biochemical components, these components can be destroyed.

Thus, a need exists to provide electrophoretic systems that, while capable of conducting viable separations, provide easy heat removal even when the process is scaled up to separations of large quantities of material. The need to remove heat effectively from both batch and continuous electrophoretic separations also is present. It should be done in an effective and uncomplicated manner.

SUMMARY OF THE INVENTION

In accordance with the instant invention an apparatus is provided which is suitable for use in conducting electrophoretic separations. It is simple in construction and permits adequate removal of heat during the separation so that the process can be conducted effectively on a batch or continuous basis. Still further, the invention provides a system that can be used for the continuous removal of the separated components of a liquid mixture undergoing electrophoresis so that the components can be collected on a continuous basis separately. Finally, the apparatus and methods provide for scale up of electrophoretic equipment to any desirable, practical extent without the deleterious effects of inadequate heat removal being experienced.

The method conducted in accordance with the instant invention involves a process in which the solution to be separated is passed through a chamber containing a plurality of closely packed hollow fibers. The fibers are packed in such a manner that interstitial spaces are provided in between the individual fibers which are of sufficient value to permit the flow of liquid through the chamber by the application of sufficient head or pumping pressure. The solution to be separated is then pumped or passed from one end of the chamber to the other at a rate sufficient to prevent or minimize the formation of convection currents in the chamber. Means are also present to supply electric current across the reaction chamber containing the packed fibers at a satisfactory voltage gradient to cause the solutions flowing therein to separate due to the difference in the electrophoretic mobility of their constituents. Further means are provided to introduce heat exchange fluid through the center of the hollow fibers to thereby allow for the cooling continuously through the chamber during the electrophoretic separation. Modified buffered solutions of the materials undergoing separations may also be provided by introduction of these solutions with those undergoing separation in individual streams or through the cooling hollow fibers by making these fibers with semi-permeable walls and feeding buffer solutions thereto as a coolant and a pH control, and achieving thereby electrofocusing. The hollow fibers in accordance with this invention perform both cooling and anti-convective functions.

BRIEF DESCRIPTION OF THE DRAWINGS

The invention will now be described with reference to specific drawings in which.

DETAILED DESCRIPTION OF THE DRAWINGS

Figure 1:
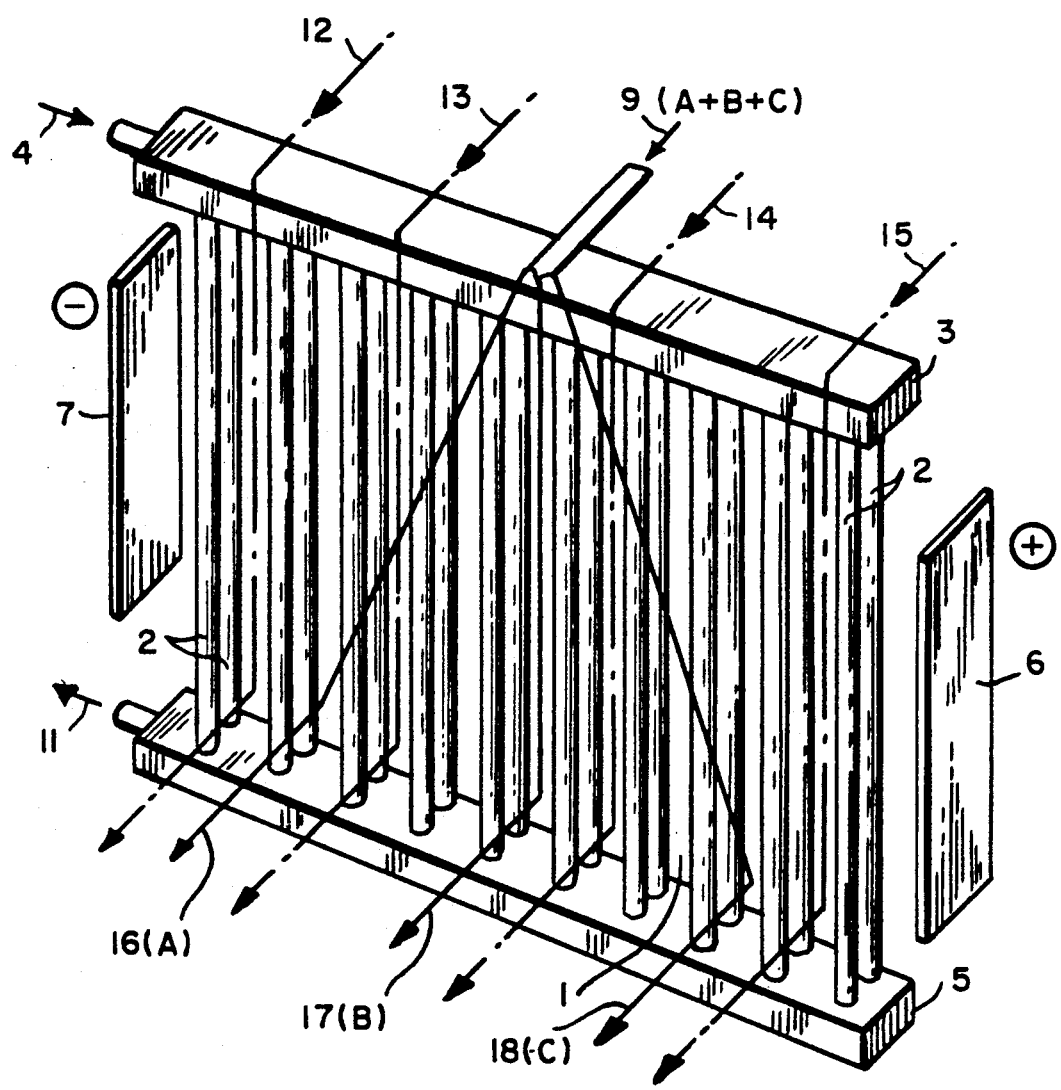
FIG. 1 shows a schematic diagram of the electrophoretic process conducted in accordance with the principles of the instant invention with the cooling tubes and electrodes being exaggerated in spacing for clarity in describing the process.

Turning to FIG. 1 there is shown an electrophoretic chamber generally indicated at 1. The chamber has a header 3 located at the top thereof which has an inlet shown by the arrow 4 on the left hand side of the Figure. Connected to the header 3 and in communication with it are a plurality of hollow fibers 2 which terminate in a collection chamber 5 located at the bottom of the device. These fibers 2 are shown separated by large spaces between them for illustration purposes only. In reality they are much closer together as will be obvious to the skilled artisan when FIG. 2 herein is discussed. The electrophoretic chamber 1 is also equipped with an anode 6 and a cathode 7 on either side of the chamber, and as indicated in the Figure, the solution to be treated flows through the device by passing it as indicated by the arrow 9 across the device from top to bottom as shown in the Figure in the interstitial spaces provided by the spacing of hollow fibers 2. The collection chamber 5 is provided with an exit 11. Also shown is the planar flow of buffer solutions to the chamber indicated by arrows 12, 13, 14 and 15 which contact solutions A, B and C. As the A, B and C solutions and buffer solutions pass through the chamber from the top to the bottom, necessary conductivity for the electrophoresis to take place is provided. By injecting buffer solutions of different pH values along the directions shown by the arrows 12 to 15, a pH gradient across the chamber can be created providing the necessary conditions for electrofocusing.

In the operation of the method in accordance with this system, solution containing material to be separated is introduced at the introduction point 9 shown in the Figure with the buffer solutions flowing at arrows 12, 13, 14 and 15. All the solutions are fed to the chamber continuously. In the chamber the solution A, B and C, which is a mixture, begins to separate upon the introduction of current at an appropriate voltage being applied between the anode 6 and the cathode 7 across the device 1 and the solution passing through it. This brings the particles of the components A, B and C into transversely directed motion based on their electrophoretic mobility causing them to separate. The components then are removed from the column on a continuous basis at the exit points 16, 17 and 18.

The arrangement of fibers 2, electrodes 6 and 7 and the electrical current between them and the flow of the solution from inlet 9 to the outlets 16, 17 and 18 are illustrative of the preferred method of operation but not of the only method that can be used to practice the invention. Thus, if desired one may pass current from electrode 6 to electrode 7 while passing heat exchange fluid through the fibers 2 in the same direction with the solution still being fed in the direction shown in FIG. 1. All that is required in this instance is the relocation of the header 3 and the chamber 5 with their associated fibers 2 in front of or behind the electrodes 6 and 7 at a 90 degree position from that shown in FIG. 1. In another arrangement that is also permitted the flow of the solution A-B-C through the electrophoretic chamber is a path which is perpendicular to the flow of the heat exchange fluid in fibers 2 and to the flow of the current between the electrodes 6 and 7. In this arrangement the header 3 and collector 5 with the fibers 2 remain in the orientation as shown in FIG. 1. The electrodes 6 and 7 also remain as shown. The solution A-B-C, however, in this embodiment is fed between the fibers from the back of the chamber to the front so that the current of the solution A-B-C and the fluid flowing in the fibers from header 3 to chamber 5 are mutually perpendicular to each other. Obviously, more rows of tubes would be required for this embodiment than shown in FIG. 1.

In another embodiment the current can be fed to the chamber 1 from electrode 6 to electrode 7 and parallel to the long axis of the fibers 2 while the solution A-B-C is also passed in parallel to both the current and the long axis of the fibers. In this embodiment the electrodes 6 and 7 would be positioned at each end of the fibers 2. It will be understood in this arrangement that the fluid flowing inside the fibers may be co-current or counter-current to the flow of the solution A-B-C.

In still another embodiment of the invention the electric current can be fed parallel to the flow of the solution A-B-C, and the fibers 2 can be arranged in the chamber 1 so that they are perpendicular to the flow of the current and the solution A-B-C. In this arrangement the electrodes 6 and 7 would be placed on opposite sides of the chamber 1. The header 3 and the chamber 5 would be placed at right angles thereto with the fibers located between them. Finally, the solution A-B-C would be fed through the chamber 1 parallel to the flow of the current.

Figure 2:
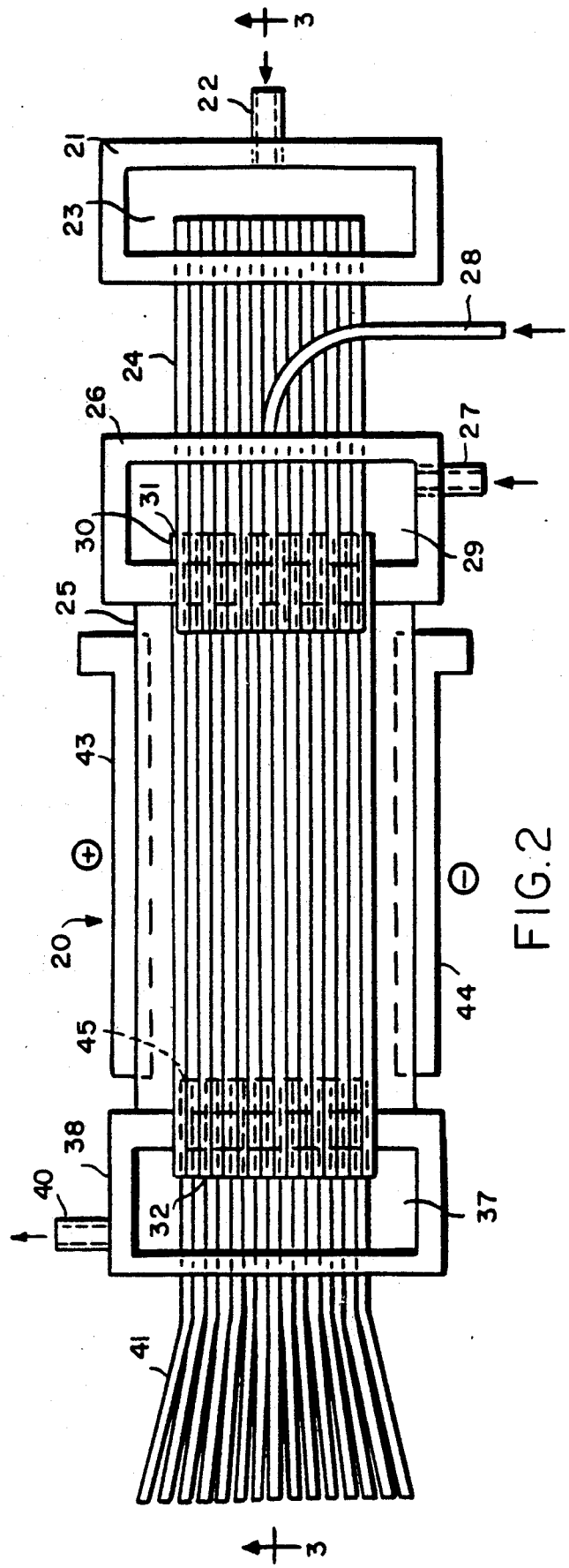
FIG. 2 shows a plan view of an apparatus suitable for use in conducting the electrophoresis process described herein.

Turning now to FIG. 2, an electrophoresis system is shown which is generally indicated at 20 and operates using the preferred embodiment regarding flow hereinafter described. This system has container 21 with a chamber 23 and fluid inlet 22. A plurality of hollow delivery tubes 24 are positioned across the chamber 23. These tubes 24 terminate in the electrophoretic chamber 25 after passing through a second container 26 which has an inlet tube 27. The inlet 27 terminates in an internal chamber 29 located in container 26 which is also in communication with a plurality of closely packed hollow capillary tubes or fibers 30 (hereinafter 'fibers') having one open end 31 in chamber 29 and the other open end 32 in chamber 37 of a third container 38. The inlet tube 28 terminates in chamber 25 like all of the tubes 24 so that the mixture of components to be separated can be injected into the common flow in chamber 25 through tube 28.

Figure 3:
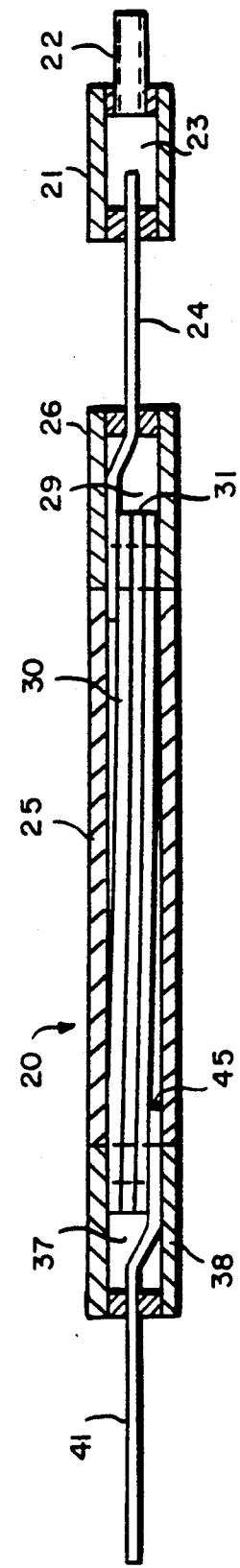
FIG. 3 is a cross section of FIG. 2 taken along the lines III—III.

The cooling fluid introduced through inlet 27 is removed from the electrophoretic chamber 25 at exit 40 shown in the upper portion of the chamber 38 in FIG. 2. The fluid or solution introduced through inlet 22 is passed into chamber 25 where is passes with the mixture of components introduced by tube 28 through the chamber 25 to outlets 41 shown at the exit end of the electrophoretic chamber 25. As can be seen more clearly in FIG. 3, the buffer solution which is introduced through tube 22 and passes through the hollow tubes 24 terminates at a point above the hollow fibers 30 located in the electrophoretic chamber 25 and thus pass through that chamber in the interstices formed between the hollow fibers 30 in their packing width-wise and depth-wise throughout the chamber 25. The separated materials are removed through a plurality of streams flowing through the interstitial spaces between tubes 41. The electrophoretic chamber 25 of the electrophoretic system 20 is also provided with an anode 43 and a cathode 44 for the application of sufficient voltage to conduct the electrophoretic separation of the components.

In general in operating the apparatus of FIG. 2 the buffer solution to be used, which can be any conventional buffer commonly employed to adjust pH, is introduced through inlet 22 and passes through the hollow tubes 24 into the electrophoretic chamber 25 in proximity to the fibers 30 shown therein. The buffer solutions fed through inlet 22 and tubes 24 are passed therethrough with sufficient head or pumping pressure to provide for continuous passage of the solutions in contact with and between the interstices of the capillary tubes 30 from one end of the electrophoretic chamber 25 to the other and with minimum turbulence being generated in the chamber 25. The solution to be separated is introduced in tube 28 to chamber 25 and, again, like the buffer solutions, is passed from one end of the chamber 25 to the other through the interstitial spaces provided by hollow fibers 30. The solution during its passage through chamber 25 is subjected to a D.C. voltage applied between anode 43 and cathode 44 which causes the material to separate into its components by virtue of differences in electrophoretic mobilities of each component. As the voltage is applied across the anode 43 and the cathode 44 and current passes through the chamber 25, the components of the solution introduced to the chamber 25 separate across the width of the chamber. The components, which are separated in accordance with their electrophoretic mobility, effectively separate into component streams.

As the solution being separated passes along the interstices of the hollow fibers 30, cooling fluid is introduced through inlet 27 into the inlet ends 31 of the hollow fibers 30 and is passed continuously along the long axis of the hollow fibers 30 into chamber 37 of the container 38 at open end 32 of the hollow fibers 30. This effectively removes the heat generated by the electrophoretic separation taking place as the solution to be separated passes through the chamber 25 and the heat exchange fluid is removed continuously through exit 40. Thus, the introduction and passage of the cooling fluid through fibers 30 and its removal at exit 40 is done on a continuous basis so that the chamber is continuously being charged with cooling solution at a regulated temperature. The heat evolution is thereby controlled, and the temperature control system eliminates overheating of the device during the passage of solutions through it. At the exit end of the electrophoretic chamber 25 a plurality of hollow tubes 41 are provided across the chamber 25, each having inlets 45 through which the separated components pass into some of the individual tubes shown. At the exit end of chamber 25 the inlets 45 of tubes 41 receive the separated components of the feed solution. The separated components may then be removed from the corresponding tubes 41.

While FIG. 2 has been described with reference to the preferred flow of solution to be separated, current flow and fiber arrangement for heat exchange, the flows described with reference to FIG. 1, can be employed without departing from the spirit of the invention so long as the separation is conducted in the interstices of the fibers 30.

The hollow fibers used for cooling may be of any convenient diameter. Preferably fibers having diameters in the range of 15 to 500 microns are used. The fibers have hollow interiors. In the preferred mode hollow polymeric fibers are utilized.

Inorganic fibers such as hollow silica and hollow glass fibers are also suitable for this purpose. Exemplary of hollow glass fibers for use in this process are those described in U.S. Pat. Nos. 3,510,393 and more recently 4,735,642, the latter patent also describing in detail various glasses that may be utilized to form the hollow glass fibers.

Exemplary of the organic fibers, which are preferred as cooling fibers 30 are polymers such as polyethylene, polypropylene, polysulfides, polycarbonates, polyethylene terephthalate, polybutylene terephthalate tetrafluoroethylene (Teflon®) and other similar polymers capable of being made into hollow fibers.

In providing sufficient space in the interstices outside of and between the cooling fibers 30 usually the packing of the round fibers 30 themselves will suffice to provide it. If desired, however, spacers may be used to insure adequate room for the electrophoresis to take place as long as they are permeable to fluid flow between the layers of fibers. These spacers can be between the fibers through the depth or width of the chamber 25 or both if desired. Suitable materials for this purpose are cloths, mats, scrims, meshes, filaments, membranes, papers and the like, provided they do not conduct electricity.

Electrodes 43 and 44 are usually housed in chamber 25 with a permeable membrane (not shown) positioned between the electrode surface and the contents of the chamber. Means (not shown) are also provided so that the electrodes can be rinsed continually with solution to remove the products of electrolysis from surrounding liquid. This is common practice in the art of which the skilled artisan will have knowledge. Solutions that can be separated into components in accordance with the instant invention are many and varied and the application of the various voltages will be determined, generally speaking, by recourse to the materials contained in the solution and their ability to separate based on their electrophoretic mobility.

In applying electric current across the solutions undergoing electrophoretic separation in accordance with the invention, the voltage utilized at a minimum is that voltage which will produce a separation in a given solution when applied across the chamber housing the solution. The maximum voltage utilizable is determined by safety factors and essentially has no bearing on the separation per se. In general, voltages of 50 to 200 volts per centimeter of distance between the electrodes (voltage gradient) are employed. A voltage gradient of 100 volts per centimeter has been found to be preferable and is used for most separations since this provides adequate separations for most solutions and minimizes safety risks.

EXAMPLES

In order to test the principles of the instant invention a model was built which consisted of four flat chambers made of plexiglass and similar to the configuration shown in FIG. 2. Tap water was utilized as both the buffer solution and the coolant in this Example, and it was introduced through inlets 27 and 22. A mixed water solution of amaranth (a red dye) and a blue food dye, which mixture had a violet color, was utilized as the mixture fed through inlet 28. Teflon® spaghetti tubing having an internal diameter of 0.015 inches and an outside diameter of 0.027 inches was utilized as the tubes 24 and 41. The electrophoretic chamber 25 had dimensions of 4.5×2×0.125 inches. The electrodes were made of stainless steel mesh. They were separated from the solution in the main chamber by pieces of glass wool filter paper. No rinsing of the electrodes was provided during the experiment. The voltage applied between electrodes 43 and 44 during the test across the 2 inch width of the electrophoretic chamber 25 was 600 volts and the flow rate of the cooling fluid passing through the chamber was 100 milliliters/hour. The cooling tubes 30 were Teflon ® spaghetti tubing having the dimensions of 0.047 inches outside diameter and an internal diameter of 0.035 inches. When voltage was applied and the cooling tubes were operative, the violet track of the mixture was separated into three overlapping tracks. A red track formed on the anode side, a blue track formed on the cathode side and an intermediate track of a reduced violet color in between. When the cooling was stopped by deliberately cutting off the supply of water through inlet 27 during the test, the intermediate track was dominating, and bubbles of air or steam appeared between the cooling tubes. The electrophoretic chamber 25 was warm to the touch. While the mixture was being cooled with a continuous flow of coolant in tubes 30, the blue and red fractions separated readily and red fractions and blue fractions were collected continuously at the outlets 41 separately from each other.

Many modifications of the invention can be made. Thus, using the device of FIG. 2, a separation can be enhanced by using a pH gradients across the electrophoretic chamber 25. For example, buffer solutions of differing pH values can be introduced into the inlets of tubes 24 individually. In this instance, the chamber 23, housing 21 and inlet 22 are no longer needed since each of the tubes 24 will be fed directly with their own respective buffer solution, which solutions will have different pH values. Ampholytes such as proteins, for example, contain both anionic and cationic groups. Usually at some pH value such proteins will have no mobility in the electrophoretic (isoelectrical point) sense. Therefore, by controlling pH across the unit by segments it is possible to concentrate the electrophoretic zone of an individual component along the pH gradient established between the electrodes by using as a control multiple buffer solutions of differing pH values. At some point along the gradient for example, one constituent will be isolated because it will have no mobility and in this way, by electrofocusing, made possible by the establishment of a given pH gradient across the chamber, that one component can be concentrated in a narrow band in the electrophoretic chamber and removed therefrom.

In another modification of the establishment of a pH gradient the hollow fibers 30 can be formed of hollow glass or organic fibers that are semi-permeable or porous with a controlled porosity that imparts membrane properties to them. If fibers are used having these characteristics, buffer solutions can be introduced into fibers 30 via inlet 31, and the fibers will function as both a cooling tube and as a source of ions to establish a pH gradient across the chamber in the solutions being separated as they pass along the fiber surfaces. Again, each fiber will be fed buffers at various pH values.

Finally, if desired, the apparatus of FIG. 2 can be altered to conduct a batch process by moving electrodes 43 and 44 and placing them at the ends of chamber 25. Thus, for example, electrode 43 could be placed at the inlet end of chamber 25 and electrode 44 at the outlet end of chamber 25. In this instance the separate inlet 28 is not necessary since all solution is fed through inlet 22 and tube 24 to chamber 25. Cooling would still be done on a continuous basis, but the solution to be separated would be injected on a batch basis. The cross section of the electrophoretic chamber can be of any desirable shape, for example, round.

While the invention has been described with reference of certain specific examples of illustrative embodiment, it is not intended to be limited thereby except insofar as appears in the accompanying claims.

I claim:

1. A system for conducting an electrophoretic separation comprising, an electrophoresis chamber having an anode and a cathode positioned across the chamber to provide current flow through said chamber, a plurality of hollow fibers packed in said chamber and passing through the chamber, said fibers having inlets and outlets, means to introduce heat exchange fluid through said fibers, means at one end of said chamber to introduce a solution to be separated, means to remove solution from the opposite end of the chamber in a plurality of streams, the packing of the fibers being arranged to provide sufficient space therebetween to permit the solution to be separated to flow from one end of the chamber to the other in the interstices provided between the fibers by the packing.

2. The system of claim 1 including spacers located between the fibers in the horizontal direction across said chamber, said spacers being permeable to fluid flow.

3. The system of claim 1 wherein spacers are provided between the fibers in the vertical direction in the chamber, the spacers being permeable to fluid flow.

4. The system of claim 1 wherein spacers are provided between the fibers in the horizontal and vertical directions in the chamber, the spacers being permeable to fluid flow.

5. The system of claim 2 wherein the spacer is selected from the group consisting of cloth, mats, scrims, meshes, filaments, permeable membranes and papers.

6. The system of claim 3 wherein the spacer is selected from the group consisting of cloth, mats, scrims, meshes, filaments, permeable membranes and papers.

7. The system of claim 4 wherein the spacer is selected from the group consisting of cloth, mats, scrims, meshes, filaments, permeable membranes and papers.

8. The system of claim 1 wherein the fibers having external diameters of 10 to 500 microns.

9. The system of claim 1 wherein means to introduce a second fluid to the interstices between the fibers is provided in said chamber.

* * * * *